(12) United States Patent
Turin

(10) Patent No.: US 7,342,042 B2
(45) Date of Patent: Mar. 11, 2008

(54) LILY OF THE VALLEY AROMACHEMICALS

(75) Inventor: Luca Turin, London (GB)

(73) Assignee: Flexitral, Inc., Chantilly, VA (US)

( * ) Notice: Subject to any disclaimer, the term of this patent is extended or adjusted under 35 U.S.C. 154(b) by 208 days.

(21) Appl. No.: 10/869,579

(22) Filed: Jun. 16, 2004

(65) Prior Publication Data
US 2005/0096476 A1   May 5, 2005

Related U.S. Application Data

(63) Continuation of application No. PCT/US02/40018, filed on Dec. 13, 2002.

(60) Provisional application No. 60/405,653, filed on Aug. 23, 2002, provisional application No. 60/389,298, filed on Jun. 17, 2002, provisional application No. 60/377,914, filed on May 3, 2002, provisional application No. 60/355,052, filed on Feb. 7, 2002, provisional application No. 60/348,580, filed on Jan. 15, 2002, provisional application No. 60/342,150, filed on Dec. 19, 2001.

(51) Int. Cl.
*A61K 31/38* (2006.01)
*C07D 333/08* (2006.01)

(52) U.S. Cl. .................... 514/438; 549/83

(58) Field of Classification Search ........... 514/428, 514/548; 548/83; 549/83
See application file for complete search history.

(56) References Cited

U.S. PATENT DOCUMENTS

| | | | |
|---|---|---|---|
| 3,549,624 A | 12/1970 | Conover et al. | |
| 3,770,836 A | 11/1973 | Comes | |
| 3,950,429 A | 4/1976 | Lamparsky et al. | |
| 4,097,531 A | 6/1978 | Bledsoe, Jr. et al. | |
| 4,151,103 A | 4/1979 | Evers et al. | |
| 4,435,428 A | 3/1984 | Boden et al. | |
| 4,521,331 A | 6/1985 | Martel et al. | |
| 4,536,583 A | 8/1985 | Mookherjee et al. | |
| 4,658,067 A | 4/1987 | Pittet et al. | |
| 5,196,224 A * | 3/1993 | Van den Heuvel et al. | 426/535 |
| 5,368,876 A * | 11/1994 | Van den Heuvel et al. | 426/535 |
| 6,051,548 A | 4/2000 | Boden et al. | |

FOREIGN PATENT DOCUMENTS

| | | |
|---|---|---|
| DE | 26 17 816 A | 11/1977 |
| EP | 0 219 146 | 4/1987 |
| EP | 0 219 146 A | 4/1987 |
| EP | 0 418 680 A | 3/1991 |
| EP | 0 801 049 A | 10/1997 |
| EP | 0 801 049 A2 | 10/1997 |
| FR | 1 393 451 | 2/1965 |
| FR | 1.393.451 | 2/1965 |
| FR | 2 543 134 A | 2/1984 |
| FR | 2 543 134 | 9/1984 |
| GB | 1061732 A1 | 3/1967 |
| GB | 1 082 364 A | 9/1967 |
| GB | 0 219 146 | 4/1987 |
| GB | EP 0 418 680 | 3/1991 |
| GB | EP 0 801 049 | 10/1997 |
| WO | WO 01/06853 | 2/2001 |
| WO | WO 01/06853 A | 2/2001 |
| WO | WO 01/06853 A2 | 2/2001 |
| WO | WO 03/053901 | 7/2003 |
| WO | WO 03/053902 | 7/2003 |

OTHER PUBLICATIONS

Tamaru, et al., Tetrahedron, vol. 35, pp. 329-340, 1979; especially p. 335.*
Weyerstahl P et al., "Olfactory Properties and Convenient Synthesis of Furans and Thiophenes related to Rose Furan and Perillene and their Isomers", Liebigs Annalen: Organic and Bioorganic Chemistry, vol. 10, Oct. 1, 1995, pp. 1849-1853, XP000608611.
Database Crossfire Beilstein, Beilstein Instiziut zur Forderung der Chemischen Wissenschaften, Frankfurt am Main, DE: XP002233853, Beilstein Registry No. 7474532 & J. Chem. Res. Miniprint, vol. 10, 1995, pp. 2364-2379.

(Continued)

*Primary Examiner*—Kamal A. Saeed
*Assistant Examiner*—Susannah Chung
(74) *Attorney, Agent, or Firm*—Womble Carlyle Sandridge & Rice

(57) ABSTRACT

Improved cyclamenaldehyde derivatives, and fragrances and flavorings including the derivatives, are disclosed. In particular, the derivatives maintain the fragrance characteristics of cyclamenaldehyde, while enhancing the odorant intensity. In addition, when present in a fragrance they heighten the effect of the remainder of the formulation. Further, they heighten the perceived intensity of other olfactory stimuli, e.g. food and ambient smells. Also disclosed are methods of making the derivatives, and articles of manufacture including the derivatives. The derivatives are prepared by replacing the phenyl moiety in cyclamenaldehyde with a thiophene moiety, which can be unsubstituted, or substituted with one or two lower alkyl, preferably isopropyl groups. The aldehyde group in cyclamenaldehyde can also be replaced with an acetal, methyl ether, nitrile or ester functionality. The acetal groups can provide the compounds with a long lasting flavor or fragrance, where the acetals slowly hydrolyze to provide the aldehyde group in cyclamenaldehyde. Examples of suitable articles of manufacture include perfumes, colognes, candles, air fresheners, and disinfectant compositions.

10 Claims, No Drawings

OTHER PUBLICATIONS

Gagniant P et al., "Recherche dans la Serie Thiophenique—I- Etude de quelques Acides Omega, 2-Thienylaliphatiques de Formule Generale: C4H3S, (CH2)n COOH", Bulletin De La Societe Chimique De France, 1948 pp. 1083-1087, XP002233849.

Tamaru Y et al., "The Palladium Catalyzed Thienylation of Allylic Alcohols with 2-and 3-Bromothiophenes and their Derivatives", Tetrahedron, vol. 35, No. 3, 1979, pp. 329-340, XP002233850.

Arena G et al., "Thermodynamics of Protonation of some Five-Membered Heteroaryl-Carboxylates, Alkanoates and Trans-Propenoates", Journal of the Chemical Society, Perkin Transactions 2, vol. 10, Oct. 1993, pp. 1941-1945, XP002233851.

Garrigues B et al., "Synthese de 2-Tert-Butylthiophenes Substitues en Position 5", Bulletin De La Societe Chimique De France, vol. 130, No. 1, 1993, pp. 58-63, XP002233852.

R. Jorritsma et al., "The chemistry of small ring compounds. Part 44[1]. Solvolysis of cyclopropyl sulfides and ethers", Recueil, Journal of the Royal Netherlands Chemical Society, 100/5, May 1981, p. 194-200.

T. Shirafuji et al., "The Reduction of *gem*-Dibromocyclopropanes by Means of Chromiun (II) Acetate or Potassium Pentacycanocobaltate", Bulletin of the Chemical Society of Japan, vol. 44, No. 1, Nov. 1971, p. 3161-3164.

P. Grieco et al., "Construction of the *gem*-Dimethylcyclopropane Unit Employing Triphenylphosphonoium Isopropylide", Tetrahedron Letters No. 36, 1972, p. 3781-3783. Pergamon Press. Printed in Great Britain.

D. Seebach et al., "Ringöffnung von Cyclopropanon-bis-methylthio-acetalen Zu Ketonen und Dimethyldisulfid in Trifluoressigsäure . . . ", Tetrahedron Letters No. 36, 1973, pp. 3509-3512. Perfamon Press. Printed in Great Britain.

M. Julia et al., "No. 309.—Transposition homoallylique avec participation . . . ", Bulletin de la Société Chimique de France 1970 No. 5., p. 1805-1815.

M. Julia et al., "No. 311.—Transposition homoallylique avec participation . . . ", Bulletin de la Société Chimique de France 1970 No. 5 p. 1805-1815.

Abstract: Beilstein Registry No. 2087248, Copyright 1988-2003 Beilstein Institut zue Foerderung der Chemischen Wissenschaften.

Abstract: Beilstein Registry No. 2085216, Copyright 1988-2003 Beilstein Institut zue Foerderung der Chemischen Wissenschaften.

Weyerstahl P et al.: "Olfactory properties and convenient synthesis of furans and thiophenes related to rose furan and perillene and their isomers" Liebigs Annalen: Organic and Bioorganic Chemistry, vol. 10, Oct. 1 1995 pp. 1849-1853, XP000608611.

Database Crossfire Beilstein Beilstein Institut zur Forderung der Chemischen Wissenschaften, Frankfurt am Main, DE; XP002233853.

Gagniant P et al: "Recherche dans la serie thiophenique.—1.—Etude de quelques acides omega.2-thienylaliphatiques de formule generale: C4H3S.(CH2)n.COOH" Bulletin de la Societe Chimique de France, 1948, pp. 1083-1087, XP002233849.

Tamaru Y et al: "The palladium catalyzed thienylation of allylic alcohols with 2- and 3-bromothiophenes and their derivatives" TETRAHEDRON, vol. 35, No. 3, 1979, pp. 329-340, XP002233850.

Arena G et al.: "Thermodynamics of protonation of some five-membered herteroaryl-carboxylates, -Alkannoates and—Trans-Propenoates", Journal of the Chemical Society, Perkin Transations 2, No. 10, Oct. 1993 pp. 1941-1945-XP002233851.

Garrigues B et al: "Synthese de 2-tert-butylthiophenes substitues en position 5" Bulletin de la Societe Chimique de France, vol. 130, no. 1, 1993, pp. 58-63, XP002233852.

Rabinowitz M H et al: "Design of selective and soluble inhibitors of tumor necrosis factor—alpha converting enzyme (TACE)" Journal of Medicinal Chemistry, vol. 44, no. 24, Nov. 22, 2001, pp. 4252-4267, XP002266978.

Tashtoush H I et al: "Free radical coupling of alkyl and aryl halides with electron-deficient alkenes mediated by chromium(II) complexes" Chemische Berichte, vol. 126, No. 7, Jul. 2, 1993, pp. 1759-1761.

Masaki Y et al: "Substrate-specific rearrangement and acetonidation of epoxy-ethers catalyzed by tetracyanoethylene" Chemistry Letters, No. 1, Jan. 1993, pp. 17-20, XP002224829 the whole article, particularly p. 18, table 1, compound 1c4.

Armstrong A et al: "Intramolecular epoxidation in unsaturated ketones and oxaziridines" Journal of the Chemical Society, Perkin Transactions 1, No. 21, Nov. 1, 2001, pp. 2861-2873, XP002224830 the whole document, particularly p. 2862, scheme 4, compound 15c.

Schulte-Elte K H et al: Photoxygenation of 3,3-dialkylsubstituted allyl alcohols. Occurence of syn preference in the ene addition of (1) 02 at E/Z-isomeric allyl alcohols Helvetica Chimica Acta, vol. 62, No. 3, Apr. 20, 1979, pp. 816-829, XP002224831 the whole document, particularly p. 819, table 2, compound 30.

Scheller M E al: "Syntheses of cyclopropyl silyl ketones" Helvetica Chimica Acta, vol. 68, No. 1, Feb. 5, 1986, pp. 44-52, XP002224832 the whole document, particularly p. 45, scheme 1, compound 8.

Rickards R. W. et al, Synthesis of four higher dipteran bisepoxide stereoisomers of the juvenile hormone III Tetrahedron Letters, vo l. 33, No. 52, Dec. 22, 1992, pp. 8137-8140, XP002224833 the whole document, particularly p. 8139, scheme 2, compound 12.

Calo V et al: >>Enantiomeric selection via 1,3-elimination. A simultaneous kinetic resolution of halohydrins and epoxides>> Tetrahedron Letters, No. 49, 1978, pp. 4963-4966, XP002224834 the whole document, particularly p. 4963, compound (IX).

Ziegler Feet al: >>Carbon-Carbon Bond Forming Reactions with Oxiranyl Radicals>> Tetrahedron Letters, vol. 37, No. 35, Aug. 26, 1996, pp. 6299-6302, XP004030674 the whole document, particularly p. 6299, scheme 1, intermediate in the oxidation of 4 to 5.

Mori N et al: >>Synthesis of (2R, 3R)-Epoxyneral, a sex pheromone of the acarid mite, Caloglyphus sp. (Astigmata: Acaridae)>> Tetrahedron Letters, vol. 36, No. 9, Feb. 27, 1995, pp. 1477-1478, XP004028605.

Sakaguchi S et al: Selective oxidation of monoterpenes with hydrogen peroxidecatalyzed by peroxotungstophosphate (PCWP) Journal of Organic Chemistry, vol. 61, No. 16, Aug. 9, 1996 pp. 5307-5311, XP002224835—the entire document, particularly p. 5308, compounds 5a and 6a.

Filliatre C et al: "Synth~se de dArivAs cyclopropaniques en sArie p-menthAnique" Comptes Rendus Hebdomadal res des Seances de L'academie des Sciences, Serie C, vol. 273, Oct. 18, 1971, pp. 1001-1004, XP002225027—the whole document.

Julia M et al: "PrAparation de composAs terpAniques et apparentAs, a partir de mAthyl cyclopropyl cAtone" Bulletin de la Societe Chimique de France, 1960, pp. 1072-1079, XP002225028 the whole document, particularly p. 1074, compounds (V), (VII) and (IX).

Taber D F et al: "Synthesis of (-)-delobanone" Journal of Organic Chemistry, vol. 66, No. 10, May 8, 2001, pp. 3423-3426, XP001233803.

Uenishi J et al: "An extremely mild desulfurization of thiiranes; an efficient transformation from geraniol to (+)- and (-)-linalool" Tetrahedron Letters, vol. 35, No. 36, 1994, pp. 6697-6700, XP001233804.

Scheller M. E. et al.: "Photochemical reactions. Photochemistry of acylsilanes: photolysis and thermolysis of cyclopropyl silyl ketones" Helvetica Chimica Acta, vol. 73, No. 4, Jun. 20, 1990, pp. 922-931.

Database XFIRE, Beilstein Registry No. 6383807.

Database XFIRE, Beilstein Registry No. 2087248.

Keiji Maruoka, Yoshimi Fukutani, Hisashi Yamamoto, Communications, "Trialkylaluminum-Alkylidene Iodide. A Powerful Cyclopropanation Agent with Unique Selectivity", Journal of Organic Chemistry, vol. 50, No. 22, 1985, pp. 4412-4414.

Gary A. Molander and Lori S. Harring, Articles, "Samarium-Promoted Cyclopropanation of Allylic Alcohols", Journal of Organic Chemistry, vol. 54, No. 15, 1989, pp. 3525-3532.

Andreja Cercek, Branko Stanovnik, Anton Stimac, and Miha Tisler "1,3-Dipolar Cycloaddition of 2-Diazopropane to Coumarin, The Synthesis-of Derivatives of /1/ Benzopyrano /4,3-c/ Pyrazol-4(3H)-one and /1/ Benzopyrano /3,4-c/ Pyrazol-4 (1H)-one" HETEROCYCLES, vol. 26, No. 9, 1987, pp. 2425-2431.

Markus E. Scheller and Bruno Frei "Photochemistry of Acylsilanes: Photolysis and Thermolysis of Cyclopropyl Silyl Ketones" Helvetica Chimica Acta, vol. 73, No. 4, 1990, pp. 922-931.

Andre B. Charette, Helene Juteau, Helene Lebel, and Carmela Molinaro "Enantioselective Cyclopropanation of Allylic Alcohols with Dioxaborolane Ligands: Scope and Synthetic Applications" Journal of the American Chemical Society, vol. 120, No. 46, 1998, pp. 11943-11952.

Turin, From Chemical Senses, 1996, vol. 21, No. 6, p. 773-791 Note: The attached reference contains p. 1-35, which correspond to the above p. 773-791.

Office Action dated May 2, 2007, for U.S. Appl. No. 10/868,489.

Office Action dated Jun, 13, 2007 for U.S. Appl. No. 10/869,579.

Taber et al., "Synthesis of (-)-Delobanone", Journal of Organic Chemistry, vol. 66 (2001) pp. 3423-3426—see schemes 1 and 2, compound 9.

Uenishi et al., "An extremely mild desulfurisation of thiiranes; An efficient transformation from geraniol to (+)- and (-)-linalool", Tetrahedron Letters, vol. 35 (1994) No. 36, pp. 6697-6700—see scheme 2, table 1.

* cited by examiner

LILY OF THE VALLEY AROMACHEMICALS

FIELD OF THE INVENTION

The present invention relates generally to the field of fragrances. More particularly, the present invention relates to improved muguet/lily-of-the valley (henceforth muguet) derivatives that provide perfumes and other fragrant articles with a fresh, green-floral, odor. These derivatives possess an odor of greater intensity, more desirable character and other useful properties. This application is a continuation of PCT/US02/40018, filed 13 Dec. 2002, which claims priority to U.S. Provisional Application Ser. Nos. 60/405,653, filed Aug. 23, 2002, Ser. No. 60/377,914, filed May 3, 2002, Ser. No. 60/389,298, filed Jun. 17, 2002; Ser. No. 60/355,052, filed Feb. 7, 2002, and Ser. No. 60/342,150, filed Dec. 19, 2001; 60/348,580, filed 15 Jan. 2002; PCT/US02/22120, filed 12 Jul. 2002; PCT/US02/22441, filed 12 Jul. 2002 and PCT/US02/26446, filed 20 Aug. 2002, the contents of each of which are hereby incorporated by reference.

BACKGROUND OF THE INVENTION

Muguet aromachemicals are a major component of many perfumes, and have a fresh, green-floral, scent. Many are based on the structure below

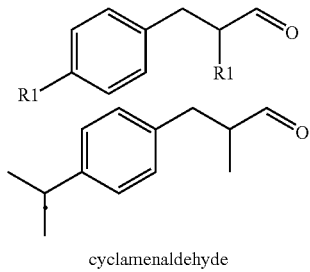

cyclamenaldehyde where R1 and R2 can be straight or branched $C_{1-5}$ alkyl chains. An example of a commonly used such material is p-isopropyl alpha-methyl dihydrocinnamaldehyde, also known as cyclamenaldehyde (henceforth, cyclamenaldehyde). It would be desirable to develop muguet derivatives with improved odorant intensity, while maintaining their fresh, floral, muguet character. The present invention provides such derivatives.

SUMMARY OF THE INVENTION

Improved fragrances and flavorings that have an increased odorant intensity relative to cyclamenaldehyde are disclosed. In particular, cyclamenaldehyde derivatives that maintain the flavor and/or fragrance characteristics of cyclamenaldehyde, while increasing the odor intensity relative to cyclamenaldehyde are disclosed. Also disclosed are methods of making the derivatives, and articles of manufacture including the derivatives.

In one embodiment, the cyclamenaldehyde derivatives are prepared by replacing the phenyl ring in cyclamenaldehyde with a thiophene ring, which can otherwise be unsubstituted, or additionally substituted at the 2 and/or 3 position with one or two lower alkyl, preferably methyl groups. The aldehyde group in cyclamenaldehyde can further be replaced with an acetal, methyl ether or nitrile functional group. Acetal groups can provide the compounds with a long lasting flavor or fragrance, where the acetals slowly hydrolyze to provide the parent aldehyde compounds. When the acetal substitution is coupled with the replacement of the phenyl ring with thiophene, which increases the odorant intensity, the cyclamenaldehyde derivatives can provide a similar odorant intensity to cyclamenaldehyde over a relatively longer period of time.

Examples of suitable articles of manufacture include perfumes and colognes, candles, air fresheners, and disinfectant compositions.

DETAILED DESCRIPTION OF THE INVENTION

Improved cyclamenaldehyde derivatives, which can be used, for example, as fragrances and flavorings that have an increased odorant intensity relative to cyclamenaldehyde, are disclosed. These cyclamenaldehyde derivatives have odor characteristics that are similar to cyclamenaldehyde. Further, in some embodiments, it has been observed that the presence of the cyclamenaldehyde derivatives actually increases the intensity of other odorants. This is apparent in two contexts: first, the presence of even low concentrations ($\leq 1\%$) of the improved derivative gives greater depth, definition and radiance to fragrance compositions of different types. Second, prolonged smelling of even low concentrations of the improved derivative heightens the sense of smell to all ambient olfactory stimuli, e.g. food, fragrances, etc.

I. Improved Cyclamenaldehydes

Formulas 1 and 2 below represent cyclamenaldehyde derivatives that can be modified using the chemistry described herein to replace the phenyl ring in cyclamenaldehyde with a thiophene ring.

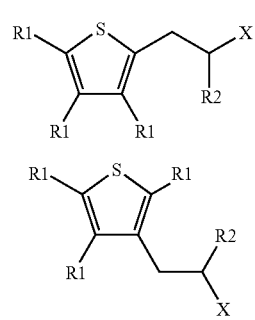

Formula 1

Formula 2

The derivative in which the phenyl ring in cyclamenaldehyde is replaced with a thiophene ring, but no other replacements are made, is shown in the above formula where X is —C(=O)H, and one of $R_1$ is an isopropyl group and the others are H, and R2=methyl. Thiophene and benzene differ in that benzene permits ortho, meta and para substitution, whereas thiophene rings offer substitution at positions one carbon and two carbons away from the ring sulfur atom. It is believed that the closest chemical analogy to cyclamenaldehyde is obtained where the carbons adjacent to the ring sulfur atom include the isopropyl and aldehyde-containing side chain present in cyclamenaldehyde. However, suitable odorants are obtained when any of $R_1$ and $R_2$ is, independently, H, $C_{1-5}$ alkyl, $C_{1-5}$ halo-substituted alkyl, or $C_{1-5}$ hydroxy-substituted alkyl, and X is —C(=O)H, —OCH$_3$, —C(OR$^7$)$_2$H, —CN, —C(=O)CH$_3$ or —C(=O)OR$^7$ (where R$^7$ is a $C_{1-5}$ alkyl).

The formula below represents a preferred cyclamenaldehyde derivative

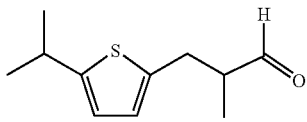

II. Methods for Preparing the Cyclamenaldehyde Derivatives

The cyclamenaldehyde derivatives of Formulas 1 and 2 can be prepared using known thiophene chemistry. For example, alkyl groups can be placed on the thiophene ring using alkyl halides and a suitable Lewis acid catalyst, for example, aluminum chloride. The aldehyde-containing side chain of cyclamenaldehyde can be attached by reacting acrolein with thiophene or an alkylated thiophene using an appropriate Lewis acid catalyst. If other aldehyde-containing side chains are desired, other olefin-containing groups can be used. Functional groups that are sensitive to the presence of Lewis acids can be protected using known protecting groups before performing the alkylation reactions, and deprotected after the alkylation reactions are complete. This can be particularly preferred if any functional groups tend to react with thiophene rings in the presence of a Lewis acid catalyst.

The aldehyde group, if present, can be protected, for example, as an acetal during the alkylation reactions, and deprotected as desired after the reactions take place. In one embodiment, however, the acetals (for example, dimethyl, diethyl, or ethylene glycol ketals) are not deprotected to the aldehyde, such that the flavoring or fragrance includes a portion of or is entirely made up of the acetals. The acetals can then slowly hydrolyze over time, releasing the muguet/lily of the valley odor.

III. Articles of Manufacture Including the Cyclamenaldehyde Derivatives

The cyclamenaldehyde derivatives can be included in virtually any article of manufacture that can include cyclamenaldehyde, or for that matter, other fragrances, whether natural or artificial. The cyclamenaldehyde derivatives are particularly well suited for use in both fine and functional perfumery. The cyclamenaldehyde derivatives can be used in applications like soaps, shampoos, body deodorants and antiperspirants, solid or liquid detergents for treating textiles, fabric softeners, detergent compositions and/or all-purpose cleaners for cleaning dishes or various surfaces, for both household and industrial use. Of course, the use of the compounds is not limited to the above-mentioned products, as they be used in other current uses in perfumery, namely the perfuming of soaps and shower gels, hygiene or hair-care products, as well as of body deodorants, air fresheners and cosmetic preparations. These uses are described in more detail below.

Perfume Compositions

The compounds can be used as perfuming ingredients, as single compounds or as mixture thereof, preferably at a range of at least about 30% by weight of the perfume composition, more preferably at a range of at least about 60% by weight of the composition. The compounds can even be used in their pure state or as mixtures, without added components. The olfactory characteristics of the individual compounds are also present in mixtures thereof, and mixtures of these compounds can be used as perfuming ingredients. This may be particularly advantageous where separation and/or purification steps can be avoided by using compound mixtures.

In all cited applications, the cyclamenaldehyde derivatives can be used alone or in admixture with other perfuming ingredients, solvents or adjuvants of current use in the art. The nature and the variety of these co-ingredients do not require a more detailed description here, which, moreover, would not be exhaustive, and the person skilled in the art will be able to choose the latter through its general knowledge and as a function of the nature of the product to be perfumed and of the desired olfactive effect.

The proportions in which the cyclamenaldehyde derivatives can be incorporated in the various products vary within a large range of values. These values depend on the nature of the article or product that one desires to perfume and the odor effect searched for, as well as on the nature of the co-ingredients in a given composition when the compounds are used in admixture with perfuming co-ingredients, solvents or adjuvants of current use in the art.

As an example, the cyclamenaldehyde derivatives are typically present at concentrations between about 0.1 and about 10%, or even more, by weight of these compounds relative to the weight of the perfuming composition in which they are incorporated. Far lower concentrations than those mentioned above can be used when the compounds are directly applied for perfuming the various consumer products cited beforehand.

The compounds can also be used in body deodorants and antiperspirants, for example, those containing aluminum salts. These embodiments are described in more detail below.

Time Release Formulations

Advantageously, all or a portion of those derivatives that include an aldehyde group can be modified to include an acetal group, which can cause the formulations to release fragrance over a period of time as the acetal hydrolyzes to form the aldehyde compound.

The present invention will be better understood with reference to the following non-limiting example.

EXAMPLE 1

Preparation of 2 & 3 Isopropyl Thiophene

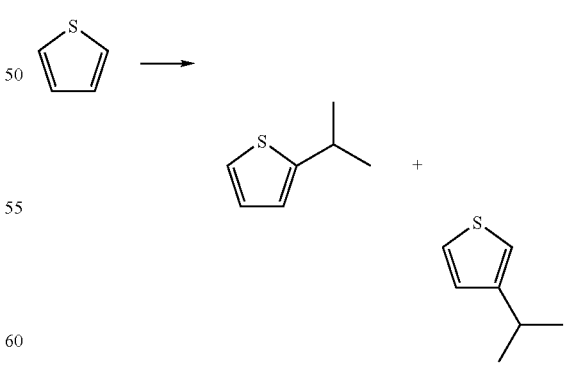

Isopropyl chloride (13 mL) was added dropwise to anhydrous aluminum chloride (23.8 g) in dry dichloromethane at −78° C. The solution was stirred for 10 minutes following the addition then thiophene (13 ml, distilled from KOH) was added (color changed to yellow). The mixture was allowed to reach room temperature as the cold bath (cardice) slowly warmed and then stirred at this temperature for 2 days (color change to red). The mixture was poured onto ice, the organic layer separated and the aqueous layer extracted with dichloromethane (2×50 mL). The combined organic layers were washed with water, 1% KOH solution and water again before drying over sodium sulfate and evaporating to dryness. Distillation at atmospheric pressure (146° C.) afforded 9 mL of the title compounds as a mixture of isomers (7:3, 2-thiophene:3-thiophene).

Alkylation of 2 & 3 Isopropyl Thiophene

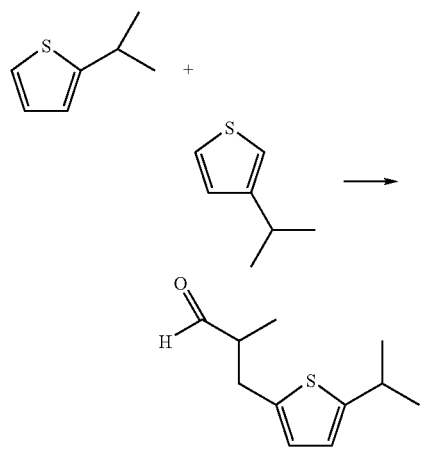

To a stirred mixture of 2-methyl acrolein (5 mL), pTSA (20 mg) and hydroquinone (20 mg) at 0° C. was added 5 mL of the above compound mixture. The solution was allowed to reach RT over 2 hours then stirred overnight. Flash column chromatography using hexane/dichloromethane (1:1) afforded the structure shown as a colorless oil (1 g).

The alkylation reaction was not optimized. The recovered starting material contained the same isomer mixture (7:3, 2-thiophene:3-thiophene) as was present at the start of the reaction.

Having hereby disclosed the subject matter of the present invention, it should be apparent that many modifications, substitutions, and variations of the present invention are possible in light thereof. It is to be understood that the present invention can be practiced other than as specifically described. Such modifications, substitutions and variations are intended to be within the scope of the present application.

What is claimed is:

1. A compound having an increased odorant intensity relative to cyclamenaldehyde and having the following formula:

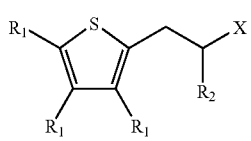

wherein each $R_1$ is independently H, $C_{1-5}$ alkyl or $C_{1-5}$ substituted alkyl, $R_2$ is $C_{1-5}$ or $C_{1-5}$ substituted alkyl, X is selected from the group consisting of —C(=O)H, —OCH$_3$, —C(OR)$_2$H (where each R is independently $C_{1-5}$ alkyl and each R is optionally covalently linked to the other R such that —C(OR)$_2$H is a cyclic acetal), —CN, —C(=O)CH$_3$ and —C(=O)OR$_7$ (where $R_7$ is a $C_{1-5}$ alkyl); excluding the compound wherein each $R_1$ is H, $R_2$ is methyl and X is COH, wherein the substituents on the substituted alkyl groups are selected from the group consisting of halo, and hydroxy.

2. The compound of claim 1, wherein $R_1$ and $R_2$ are, independently, H, $C_{1-5}$ alkyl or $C_{1-5}$ substituted alkyl, X is selected from the group consisting of —C(=O)H, —OCH$_3$, —C(OR$_2$)H (where each R is independently $C_{1-5}$ alkyl and each R is optionally covalently linked to the other R such that —C(OR$_2$)H is a cyclic acetal), —CN, —C(=O)CH$_3$ and —C(=O)OR$_7$ (where $R_7$ is a $C_{1-5}$ alkyl), wherein the substituents on the substituted alkyl groups are selected from the group consisting of halo, and hydroxy, and wherein at least one $R_1$ is isopropyl.

3. The compound of claim 1, wherein X is a nitrile, methyl ether or acetal group.

4. A compound of the formula:

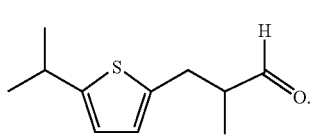

FORMULA III

5. A composition comprising a compound of formula I, as defined in claim 1, wherein each $R_1$ and $R_2$ are, independently, H, $C_{1-5}$ alkyl or $C_{1-5}$ substituted alkyl, X is selected from the group consisting of —C(=O)H, —OCH$_3$, —C(OR)$_2$H (where each R is independently $C_{1-5}$ alkyl and each R is optionally covalently lined to the other R such that —C(OR)$_2$H is a cyclic acetal), —CN, —C(=O)CH$_3$ and —C(=O)OR$_7$ (where $R_7$ is a $C_{1-5}$ alkyl), and wherein the substituents on the substituted alkyl groups are selected from the group consisting of halo, and hydroxy, together with other perfuming ingredients, solvents, or adjuvants of current use in the art of perfumery.

6. The composition of claim 5, wherein at least one $R_1$ is isopropyl.

7. The composition of claim 5, wherein X is a nitrile, methyl ether or acetal group.

8. The composition of claim 5, wherein the compound is of formula III.

9. The composition of anyone of claims 5 to 8, wherein the compound is present in an amount of at least 30 percent by weight.

10. The composition of claim 9, wherein the compound is present in an amount of at least 60 percent by weight.

* * * * *